United States Patent
Paz et al.

(10) Patent No.: US 8,663,128 B2
(45) Date of Patent: *Mar. 4, 2014

(54) DIAGNOSTIC METHOD AND APPARATUS

(75) Inventors: Ilan Paz, Gush Etzion (IL); Natan Paz, Gush Etzion (IL)

(73) Assignee: Flowsense Ltd., Misgav (IL)

( * ) Notice: Subject to any disclaimer, the term of this patent is extended or adjusted under 35 U.S.C. 154(b) by 671 days.

This patent is subject to a terminal disclaimer.

(21) Appl. No.: 12/514,835

(22) PCT Filed: Nov. 8, 2007

(86) PCT No.: PCT/IL2007/001375

§ 371 (c)(1),
(2), (4) Date: Aug. 9, 2010

(87) PCT Pub. No.: WO2008/059483

PCT Pub. Date: May 22, 2008

(65) Prior Publication Data

US 2011/0046516 A1 Feb. 24, 2011

(30) Foreign Application Priority Data

Nov. 14, 2006 (IL) .......................................... 179252
Nov. 1, 2007 (IL) .......................................... 187080

(51) Int. Cl.
*A61M 1/00* (2006.01)
*A61B 5/00* (2006.01)

(52) U.S. Cl.
USPC ......... 600/573; 600/581; 604/503; 73/861.41

(58) Field of Classification Search
USPC .................. 600/573, 581; 604/503; 73/861.41
See application file for complete search history.

(56) References Cited

U.S. PATENT DOCUMENTS

| | | | |
|---|---|---|---|
| 3,641,543 A | 2/1972 | Rigby | |
| 3,712,132 A | 1/1973 | Thys et al. | |
| 3,859,854 A | 1/1975 | Dye et al. | |
| 3,870,065 A | 3/1975 | Minns, Jr. | |
| 3,871,229 A | 3/1975 | Fletcher | |
| 3,940,742 A * | 2/1976 | Hudspeth et al. | 600/301 |
| 4,038,982 A | 8/1977 | Burke et al. | |
| 4,051,431 A | 9/1977 | Wurster | |
| 4,053,951 A * | 10/1977 | Hudspeth et al. | 600/301 |
| 4,099,412 A | 7/1978 | Nehrbass | |
| 4,116,228 A * | 9/1978 | Hudspeth et al. | 600/537 |

(Continued)

FOREIGN PATENT DOCUMENTS

| | | |
|---|---|---|
| JP | H02151724 | 12/1998 |
| JP | H04032035 | 1/2006 |

(Continued)

OTHER PUBLICATIONS

Brazilian Application P10008757-2 Office Action.

(Continued)

*Primary Examiner* — Sean Dougherty
(74) *Attorney, Agent, or Firm* — Graeser Associates International Inc; Dvorah Graeser

(57) ABSTRACT

The present invention provides a diagnostic method comprising continuously monitoring and transmitting urine output and urine flow rates of a catheterized patient to means which correlate the same with at least one of renal perfusion, renal function, fluid status, polyuria, oleguria, hypoperfusion, hemorrhage shock and GFR.

17 Claims, 13 Drawing Sheets

(56) References Cited

U.S. PATENT DOCUMENTS

| | | | |
|---|---|---|---|
| 4,125,111 A * | 11/1978 | Hudspeth et al. | 600/502 |
| 4,261,388 A | 4/1981 | Shelton | |
| 4,286,590 A * | 9/1981 | Murase | 604/30 |
| 4,291,692 A * | 9/1981 | Bowman et al. | 604/31 |
| 4,321,461 A | 3/1982 | Walter, Jr. et al. | |
| 4,325,483 A | 4/1982 | Lombardo et al. | |
| 4,343,316 A | 8/1982 | Jespersen | |
| 4,448,207 A | 5/1984 | Parrish | |
| 4,484,582 A | 11/1984 | Rottenberg et al. | |
| 4,520,667 A | 6/1985 | Nelson | |
| 4,532,936 A | 8/1985 | LeVeen et al. | |
| 4,554,687 A | 11/1985 | Carter et al. | |
| 4,559,831 A | 12/1985 | Prestele | |
| 4,650,464 A | 3/1987 | Ruiz et al. | |
| 4,683,748 A | 8/1987 | Carter | |
| 4,718,896 A | 1/1988 | Arndt et al. | |
| 4,740,200 A | 4/1988 | Theeuwes | |
| 4,827,766 A | 5/1989 | Nelson | |
| 4,936,828 A | 6/1990 | Chiang | |
| 4,946,439 A | 8/1990 | Eggers | |
| 5,098,408 A | 3/1992 | Tarzian | |
| 5,186,057 A | 2/1993 | Everhart | |
| 5,267,978 A | 12/1993 | Dirr, Jr. | |
| 5,571,964 A | 11/1996 | Sawada et al. | |
| 5,581,026 A | 12/1996 | Sawada et al. | |
| 5,698,793 A | 12/1997 | Carmichael | |
| 5,769,087 A | 6/1998 | Westphal et al. | |
| 5,840,696 A | 11/1998 | Lippton | |
| 6,372,506 B1 | 4/2002 | Norton | |
| 6,447,684 B2 | 9/2002 | Parekh et al. | |
| 6,640,649 B1 | 11/2003 | Paz | |
| 7,563,243 B2 | 7/2009 | Mendels | |
| 7,736,354 B2 * | 6/2010 | Gelfand et al. | 604/503 |
| 7,758,562 B2 * | 7/2010 | Gelfand et al. | 604/503 |
| 7,837,667 B2 * | 11/2010 | Gelfand et al. | 604/503 |
| 8,337,411 B2 * | 12/2012 | Nishtala et al. | 600/561 |
| 2002/0161314 A1 | 10/2002 | Sarajarvi | |
| 2003/0045840 A1 | 3/2003 | Burko | |
| 2006/0052764 A1 | 3/2006 | Gelfand et al. | |
| 2006/0100743 A1 | 5/2006 | Townsend et al. | |
| 2006/0253064 A1 * | 11/2006 | Gelfand et al. | 604/31 |
| 2010/0022967 A1 | 1/2010 | Mendels | |

FOREIGN PATENT DOCUMENTS

| | | |
|---|---|---|
| WO | WO0042394 | 7/2000 |
| WO | WO2004045704 | 6/2004 |
| WO | WO2006077578 | 7/2006 |
| WO | WO2010041458 | 12/2010 |
| WO | WO2010041563 | 12/2010 |

OTHER PUBLICATIONS

International Search Report for PCT/IL2006/000065.
Written Opinion for PCT/IL2006/000065.
Chinese application 201010002058.1 Office Action.
Japanese application 2007-551812 Office Action.
International search Report for PCT/IL2000/000027.
International Search Report for PCT/IL2007/001375.
International Preliminary Report on Patentability for PCT/IL2007/001375.

* cited by examiner

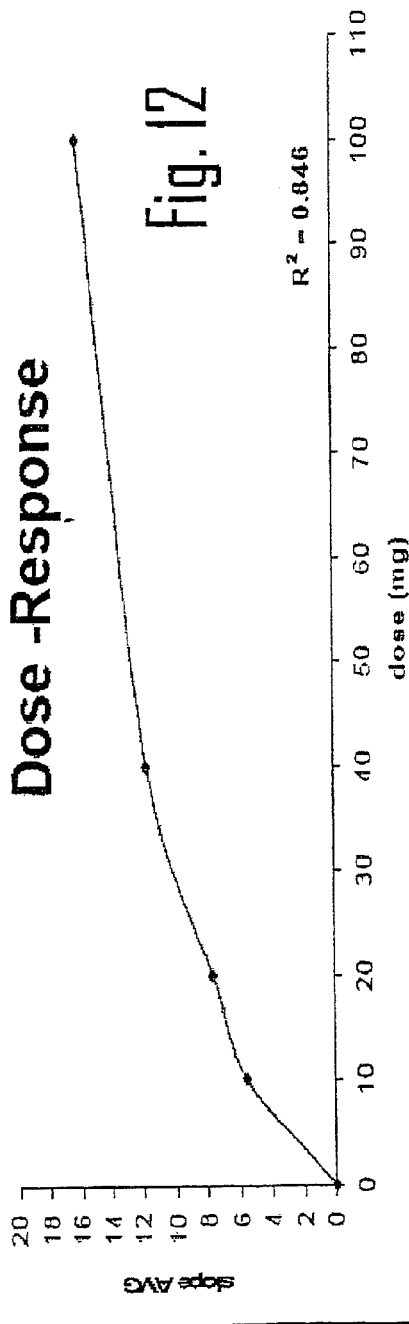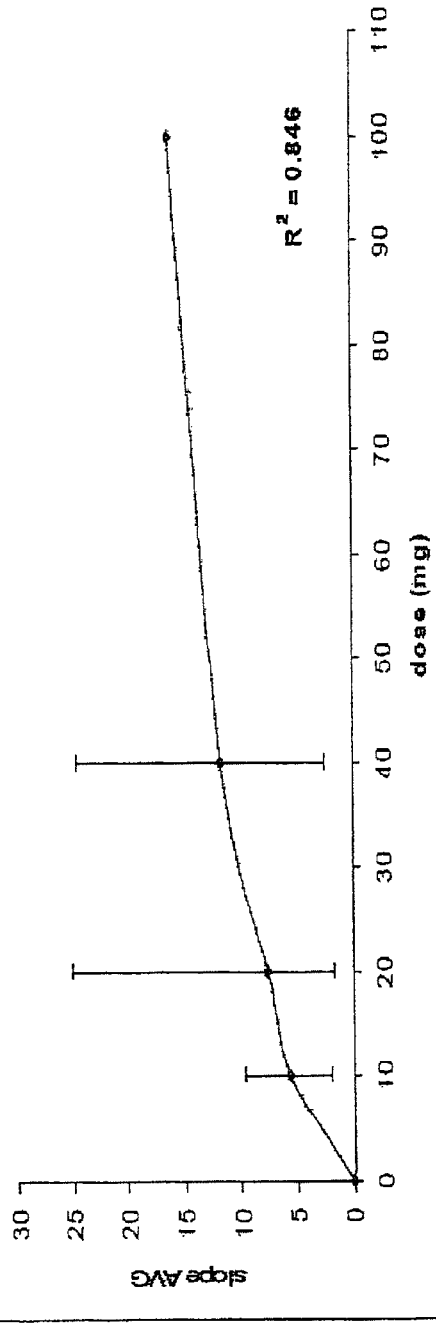
Fig. 12

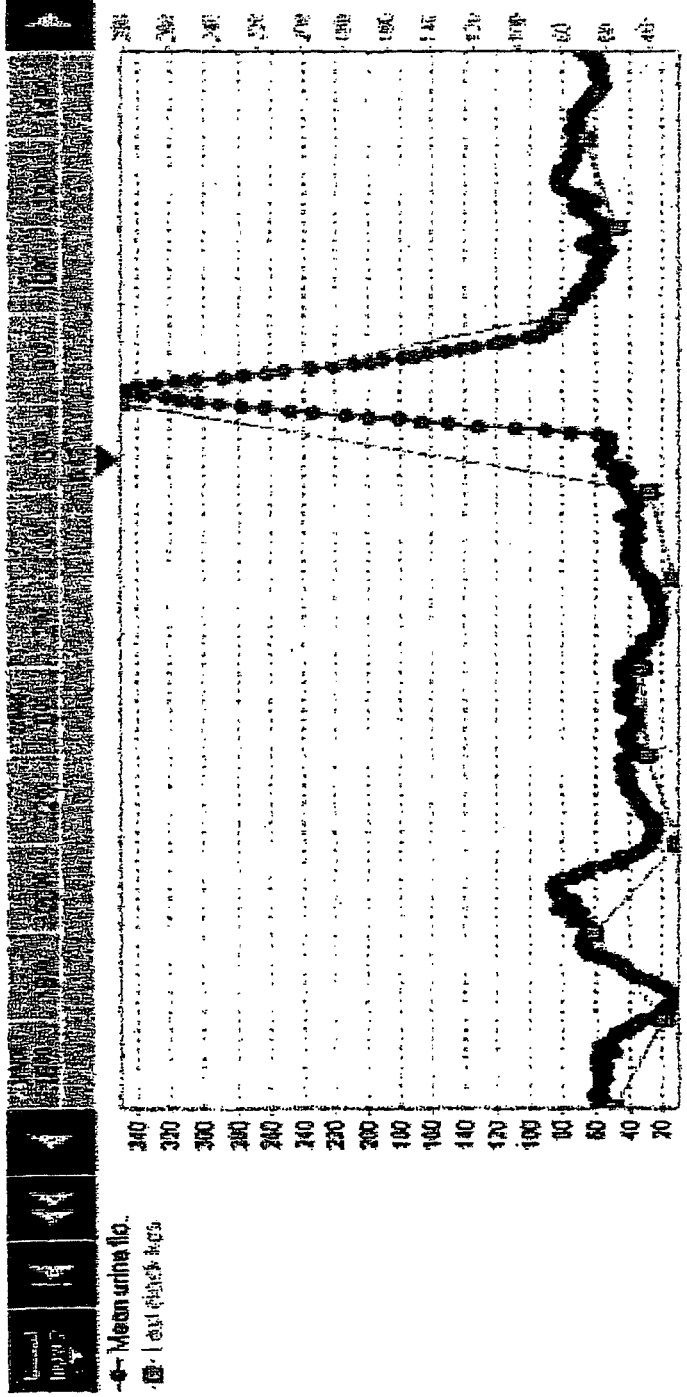

DIAGNOSTIC METHOD AND APPARATUS

The present invention relates to a diagnostic method correlating urine output and urine flow for early prognosis of a disease affiliated with abnormal body fluid status. The present invention also provides an apparatus and system for management of the hemodynamic state and kidney function of the body.

The field of the invention relates to management of a patient's fluid, more specifically providing an indication of "urine flow" such as an indication of renal perfusion, an indication of Glomerular Filtration Rate (GFR), changes in extracellular fluid, kidney function and urine irrigation problems, etc.

One of the most troublesome of all problems in critically ill patients is maintenance of adequate body fluid and proper balance between fluid input and fluid output. To date, most patients that are hospitalized in the Intensive Care Unit (ICU) are monitored by continuous measurement of several hemodynamic parameters, such as heart rate, invasive blood pressure measurement, central venous pressure (CVP) and occasionally, wedge pressure.

It is well known that one of the most important parameters that reflect proper organ perfusion is the hourly urine output. However, currently the tools and systems that are used are not precise enough. One outcome of this is the high occurrence of acute renal failure (ARF) in ICU's. This complication occurs in a significant percentage of critically ill patients. The most common underlying etiology is acute tubular necrosis, usually precipitated by hypoperfusion and/or nephrotoxic agents. On the other hand, overzealous use of fluid may result in fluid overload, pulmonary edema and ARDS.

Since appropriate management of the fluid balance and kidney function in the critically ill patient is essential it is an object of the present invention to provide a new diagnostic method that continuously monitors and measures urine output and urine flow and correlates the same to provide real time warning with regard to abnormal fluctuations and perfusion to all the organs of the body and especially the kidneys.

Thus according to the present invention there is now provided a diagnostic method comprising continuously monitoring and transmitting urine output and urine flow rates of a catheterized patient to means which correlate the same with at least one of renal perfusion, renal function, fluid status, polyuria, oleguria, hypoperfusion, hemorrhage shock and GFR.

In preferred embodiments of the present invention, said method utilizes a low flow metering device.

In especially preferred embodiments of the present invention said low flow metering device incorporates a drop generator and a droplet counter.

In a most preferred embodiment of the present invention, the present invention utilizes a modified version of the low flow metering device described and claimed in U.S. Pat. No. 6,640,649, the relevant teachings of which are incorporated herein by reference.

Preferably said method further comprises continuously monitoring and graphically representing, in real minute unit time, fluctuations in renal flow and renal output.

The method of the present invention is especially useful for early prognosis of a disease affiliated with abnormal body fluid status and kidney stress in medical procedures such as surgery as well as being useful for providing an indicator of active nephron mass and kidney function.

As will be realized the method of the present invention is useful for detecting a disease affiliated with hypoperfusion.

The present invention is also useful for detecting a disease affiliated with hyperperfusion.

In especially preferred embodiments of the present invention said method further comprises providing alarm means.

Another aspect of the present invention relates to the use of a low flow metering device for the manufacture of a diagnostic apparatus for continuous monitoring and measuring of urine, output and urine flow of a catheterized patient further comprising linking the output of said device with means which correlate the same with at least one of renal perfusion, renal function, fluid status, polyuria, oleguria, hypoperfusion, hemorrhage shock and GFR.

In especially preferred embodiments of the present invention, there is provided a diagnostic method comprising monitoring and transmitting urine flow rates per minute units of a catheterized patient to means which correlate the same with at least one of renal perfusion, renal function, fluid status, polyuria, oleguria, hypoperfusion, hemorrhage shock and GFR.

The term "urine flow rates per minute units" as used herein, is intended to denote that in the apparatus and system of the present invention the volume of urine flow per a predetermined average of time intervals of minute units, such as every three minutes, is plotted on a graph.

In contradistinction to prior art systems, the present invention provides real time information in terms of minute units and thus provides real time information in less than 30 minutes, preferably less than 20 minutes, and most preferred, in some of its aspects and utilizations, provides useful and critical information in less than 10 minutes.

In a most preferred embodiment of the present invention there is provided a diagnostic method for determining the hemodynamic state of a patient comprising administering a diuretic to a catheterized patient and monitoring and displaying the slope of urine output per minute units after administration thereof.

In another preferred embodiment of the present invention there is provided a diagnostic method for determining the hemodynamic state of a patient comprising administering a bolus of fluid to the patient and monitoring and displaying urine flow reaction to said bolus to determine the state of hydration and hemorrhagic shock.

The diagnostic method of the present invention allows for both the continuous monitoring and transmission of urine output and flow rate information regarding a catheterized patient to means which correlate and display the same in real time, and will be integrated into an apparatus and system supplied to hospitals and other patient care facilities capable of showing an online and visual trend of urine output as well as a new clinical parameter, namely "urine flow". This parameter is generated by online and continuous monitoring of urine production by the kidneys.

Another aspect of the present invention, is directed to the use of a low flow metering device for the manufacture of a diagnostic system for continuous monitoring and measuring of urine output and urine flow of a catheterized patient further comprising linking the output of said device with means which correlate the same with at least one of renal perfusion, renal function, fluid status, polyuria, oleguria, hypoperfusion, hemorrhage shock and GFR.

In another aspect of the present invention, there is provided a system for management of the hemodynamic state and kidney function of the body comprising a low flow metering device which continuously monitors and measures urine output and urine flow of a catheterized patient wherein the output of said device is linked to monitoring means and displaying means which display the slope of urine output and urine flow rates per minute units.

The present invention also provides an apparatus for management of the hemodynamic state and kidney function of the body comprising a low flow metering device which continuous monitors and measures urine output and urine flow of a catheterized patient wherein the output of said device is linked to means for monitoring and displaying the slope of urine output and urine flow rates per minute units.

As is known, often the treating physicians are faced with a patient or body in a state of unconsciousness, semi-consciousness, or lack of control, as a result of a disease or trauma or induced by the medical staff, said patient being in the operating room, the ICU, the CCU, or in another critical care situation. When the body is in a steady state, and the kidneys are properly functioning with no blockages, and when the fluid flow into the body is constant, such as a result of IV or IV pumps, then the amount of urine produced is constant and there is a continuous urine flow which is also constant.

Once it has been ascertained that the kidney is capable of producing urine at a specific flow rate, then the urine flow rate can be maintained by maintaining the fluid flow rate into the body as a constant.

A rule of thumb usually accepted by most doctors establishes a urine production rate of 1 ml/kg/hr.

A specific urine flow rate can then be calculated for a patient and fluid input can be adjusted and urine flow rate measured in order to establish this specific urine flow rate. As long as this fluid input rate is maintained and the kidneys continue to properly function, the urine flow rate will remain constant and the hydration of a patient can be managed accordingly.

By providing the apparatus of the present invention wherein the urine flow rate is graphically represented in real minute unit times, it is possible to immediately detect and deal with kidney stress and kidney malfunction, which have now been found to be accurate and early indicators of body dysfunction.

In preferred embodiments of the present invention said apparatus further comprises means which correlate the same with at least one of renal perfusion, renal function, fluid status, polyuria, oleguria, hypoperfusion, hemorrhage shock and GFR.

Preferably, said apparatus further comprises means for continuously monitoring and graphically representing in real minute unit time fluctuations in renal flow and renal output.

In some preferred embodiments of the present invention said apparatus comprises means for monitoring and measuring of urine output and urine flow of a catheterized patient after the administration of a diuretic.

In other preferred embodiments of the present invention said apparatus comprises means which monitors and measures urine output and urine flow of a catheterized patient after the administration of a bolus of fluid to a patient in a stable steady state with a constant fluid input and output.

In especially preferred embodiments of the present invention there is provided an apparatus for management of the hemodynamic state and kidney function of the body comprising a low flow metering device for continuous monitoring and measuring of urine output and urine flow of a catheterized patient wherein the output of said device is linked to means for monitoring and displaying the slope of urine output and urine flow rates per minute units during surgery.

In other preferred embodiments of the present invention there is provided an apparatus for management of the hemodynamic state and kidney function of the body comprising a low flow metering device which continuously monitors and measures urine output and urine flow of a catheterized patient, wherein the output of said device is linked to means which monitor and display the slope of urine output and urine flow rates per minute units after administration of a nephrotoxic drug.

In yet another preferred embodiments of the present invention there is provided an apparatus for management of the hemodynamic state and kidney function of the body comprising a low flow metering device for which continuously monitors and measures urine output and urine flow of a catheterized patient wherein the output of said device is linked to means which monitor and display the slope of urine output and urine flow rates per minute units during administration of a nephrotoxic drug As is known, in most catheterized patients measurement of urine output is performed by an hourly assessment of the urine volume in a canister or by electronically measuring the volume in a canister. In contradistinction, by providing reliable, high resolution and continuous trends of the patient's "urine flow", the present invention enables continuous online provision of an indication of renal perfusion, renal function, fluid status, polyuria, oliguria and GFR.

The goal of the present invention is to continuously monitor and display in real time the urine flow in order to optimize fluid management thereby enabling early prognosis of disease affiliated with Hypoperfusion such as ARF caused by renal Hypoperfusion, Intrinsic ARF and Postrenal azotemia etc. and Hyperperfusion such Edema, the use of diuretics etc.

It is to be noted that with the tools available in a standard emergency room and ICU, there is no way to immediately check for hemorrhage shock or hypoperfusion of an admitted patient.

As is known, blood pressure does not reflect blood loss, since in the case of blood loss vasoconstriction cuts off the arterioles in less vital organs as perceived by the brain, i.e., the legs, the arms, the stomach and even the kidney, in order to maintain blood flow and blood pressure to the brain. It is for this reason that up to 35% of patients in an ICU unit suffer from acute kidney injury since the monitoring teams have no way of knowing that blood has been cut off from the kidney when the patient is in a hypoperfusion state, or is suffering from kidney damage as a result of drugs which act as nephrotoxins.

Thus, many drugs, and especially anti-cancer drugs, function as nephrotoxins.

It has now been found, according to the present invention, that by measuring urine flow, one can tell when the kidney is in stress and based thereon, treatment with said drug can be slowed whereby the drug is administered in a regulated way in order to limit kidney damage such as by administering the drug over a 4 hour period instead of in a single immediate dose.

Today, creatinine is used as a measure of kidney state, however, creatinine in the blood occurs when the kidney cannot remove some or all of the creatinine from the body, and this occurs only when there is already between about 50%-70% kidney damage. Thus the creatinine test is ineffective for showing kidney damage of up to and even greater than 50%.

As is known, the rise of creatinine in the blood as a result of kidney damage takes hours and even days to occur and therefore the creatinine test gives its results much too late to reverse kidney damage.

It has now been found that with early detection of kidney damage, i.e., within the first half hour or so, the damage can be reversed by corrective action, or at a later stage, e.g., within 1-1.5 hours, can be reversed with certain drugs and therefore there is a need for a marker providing early detection of renal failure, also known as AKI (acute kidney injury).

According to the present invention, it has now been discovered that administration of a loop diuretic such as Fusid (furosamide) to a patient, results in a rise in the flow rate of urine per minute units which can be plotted on a graph and the slope of which is a linear slope. Thus it has now been discovered that this slope is proportional to the peak flow rate of urine which is proportional to the total volume of urine produced as a result of the administration of a diuretic which in turn is proportional to the state of the kidney in terms of active nephron mass and which slopes therefore represent the percent of damage to the kidney. Therefore displaying and noting the linear slope in a graph generated in a relatively short period of time e.g., in the first 5 minutes after administration or a similarly chosen minute time unit, is sufficient to establish a clear picture of kidney function.

Similarly it is possible to effect a fluid challenge to the body, e.g., by administering a predetermined amount of fluid to the system, such as 200-300 ml, and then monitoring and displaying the slope of urine output per minute unit after administration thereof, wherein either the slope, the peak or the total time for the flow of urine to return to steady state flow, serves to determine the state of the kidney and the existence or absence of hemorrhagic shock in a patient.

Thus in a preferred embodiment of the present invention, there is provided a diagnostic method for determining the hemodynamic state of a patient comprising administering a bolus of fluid to the patient and monitoring and displaying urine flow reaction to said bolus to determine the state of hydration and hemorrhagic shock.

Thus the present invention provides a novel and greatly needed tool for early detection of kidney damage and the degree thereof, thereby enabling the timely treatment for reversing the same As a side benefit of the present invention, it has been discovered that it is not necessary to administer large doses such as 500 mg of a diuretic such as Fusid, since diuretic drugs are known to be nephrotoxins and it is sufficient to administer a smaller dose of 40-50 mg in order to obtain the same effect.

According to the present invention, it is now possible to monitor and display kidney function during surgery and to detect kidney stress in real time, in minute units during surgery, whereby the surgeon then has a much earlier indicator, than presently available, that corrective action is immediately required.

The following is a partial list of diseases that are associated with and indicated by abnormal urine flow: kidney perfusion, renal failure, organ perfusion, pre-operative/post-operative complications, surgical success, undetected internal trauma, dehydration, response to medication (antibiotics, diuretics etc), jaundice, shock, preeclampsia, bladder infection, cystitis, prostatitis, urinary tract infection, kidney stones, low blood pressure, anuria (lack of urine), hypovolemia, hypervolemia, pulmonary edema, and hyponatremia, The following are explanations of terms and diseases referred to herein.

ARF (Acute Renal Failure)

Acute Renal Failure (ARF) is a syndrome characterized by rapid decline in glomerular filtration rate (hours to days), retention of nitrogenous waste products, and perturbation of extracellular fluid volume and electrolyte and acid-base homeostasis. ARF complicates approximately 5% of hospital admissions and up to 30% of admissions to intensive care units. Oliguria (urine output<400 mL/d) is a frequent but not invariable clinical feature (50%). ARF is usually asymptomatic and diagnosed when biochemical monitoring of hospitalized patients elevates a recent increase in blood urea and creatinine concentrations. It may complicate a wide range of diseases, which for purposes of diagnosis and management are conveniently divided into three categories:

(1) Diseases that cause renal hypoperfusion without compromising the integrity of renal parenchyma (prerenal ARF, prerenal azotemia) (55%),
(2) Diseases that directly involve renal parenchyma (intrinsic renal ARF, renal azotemia) (40%);
(3) Diseases associated with urinary tract obstruction (postrenal ARF, postrenal azotemia) (5%).

Most ARF is reversible, the kidney being relatively unique among major organs in its ability to recover from almost complete loss of function. Nevertheless, ARF is associated with major in-hospital morbidity and mortality, in large part due to the serious nature of the illnesses that precipitate the ARF. Severe cases may show clinical or pathologic evidence of ATN. Contrast nephropathy classically presents as an acute (onset within 24 to 48 h) but reversible.

GFR

The GFR was originally determined by injecting inulin into the plasma. Since inulin is not reabsorbed by the kidney after glomerular filtration, its rate of excretion is directly proportional to the rate of filtration of water and solutes across the glomerular filter. In clinical practice however, creatinine clearance is used to measure GFR. Creatinine is an endogenous molecule, synthesized in the body, which is freely filtered by the glomerulus (but also secreted by the renal tubules in very small amounts). Creatinine clearance is therefore a close approximation of the GFR. The GFR is typically recorded in milliliters per minute (ml/min).

Example: A person has a plasma creatinine concentration of 0.01 mg/ml and in 1 hour he excretes 75 mg of creatinine in the urine. The GFR is calculated as M/P (where M is the mass of creatinine excreted per unit time and P is the plasma concentration of creatinine).

$$GFR = \frac{\frac{75 \text{ mg}}{60 \text{ mins}}}{0.01 \text{ mg/ml}} = 125 \text{ ml/min}$$

Chronic Renal Failure (CRF) develops slowly and gives few symptoms initially. It can be the complication of a large number of kidney diseases, such as IgA nephritis, glomerulonephritis, chronic pyelonephritis and urinary retention. End-stage renal failure (ESRF) is the ultimate consequence, in which case dialysis is generally required until a donor for a renal transplant is found.

Acute Renal failure (ARF) is, as the name implies, a rapidly progressive loss of renal function, generally characterised by oliguria (decreased urine production, quantified as less than 400 mL per day in adults,[1] less than 0.5 mL/kg/h in children or less than 1 mL/kg/h in infants), body water and body fluids disturbances and electrolyte derangement. An underlying cause must be identified to arrest the progress, and dialysis may be necessary to bridge the time gap required for treating these underlying causes Acute renal failure can be present on top of chronic renal failure. This is called acute-on-chronic renal failure (AoCRF). The acute part of AoCRF may be reversible and the aim of treatment, like in ARF, is to return the patient to their baseline renal function, which is typically measured by serum creatinine. AoCRF, like ARF, can be difficult to distinguish from chronic renal failure, if the patient has not been followed by a physician and no baseline (i.e., past) blood work is available for comparison.

Before the advancement of modern medicine renal failure might be referred to as uremic poisoning. Uremia was the term used to describe the contamination of the blood with urine. Starting around 1847 this term was used to describe reduced urine output, now known as oliguria that was thought to be caused by the urine mixing with the blood instead of being voided through the urethra.

Prerenal azotemia is relatively common, especially in hospitalized patients. The kidneys normally filter the blood. When the volume or pressure of blood flow through the kidney drops, blood filtration also drops drastically, and may not occur at all. Waste products remain in the bloodstream and little or no urine is formed, even though the internal structures of the kidney are intact and functional.

Lab tests show that nitrogen-type wastes, such as creatinine and urea, are accumulating in the body (azotemia). These waste products act as poisons when they accumulate, damaging tissues and reducing the ability of organs to function. The build-up of nitrogen waste products and accumulation of excess fluid in the body are responsible for most of the symptoms of prerenal azotemia and acute renal failure.

Prerenal azotemia is the most common form of kidney failure seen in hospitalized patients. Any condition that reduces blood flow to the kidney may cause it, including loss of blood volume, which may occur with dehydration, prolonged vomiting or diarrhea, bleeding, burns, and other conditions that allow fluid to escape from circulation.

Conditions in which the volume is not lost, but in which the heart cannot pump enough blood, or the blood is pumped at low volume, also increase risk for prerenal azotemia. These conditions include shock (such as septic shock), heart failure, and conditions where the blood flow to the kidney is interrupted, such as trauma to the kidney, surgery of various types, renal artery embolism, and other types of renal artery occlusion.

Thus it will be realized that the method of the present invention provides the ICU and other medical facilities and departments with a valuable new diagnostic tool heretofore not available.

While the invention will now be described in connection with certain preferred embodiments in the following examples and with reference to the attached figures so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

In the figures,

FIG. 12 is a graphical representation of urine flow output as related to dose of diuretic drug administered; and FIG. 13 is a graphical representation of urine flow as a function of time when a body is in a stable state and when a bolus of fluid is administered.

Figure 1:
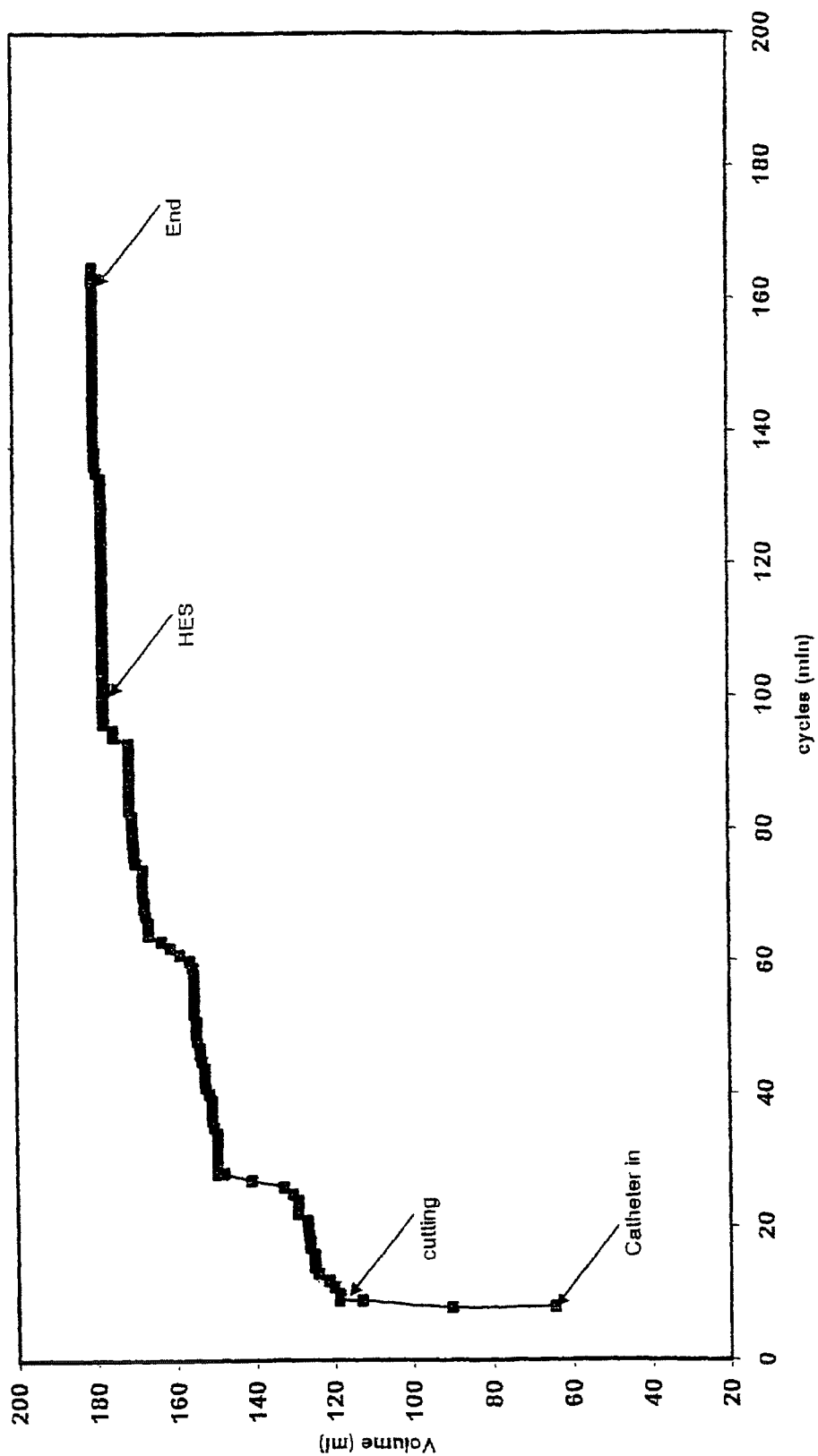
FIG. 1 is a graphical representation of urine volume measured by prior art methods during open heart surgery of a patient.

Referring now to FIG. 1, there is seen a graphical representation of urine volume over time of a patient during open heart surgery wherein according to the graph, there is a constant increase in volume and therefore no problems are detected.

Figure 2:
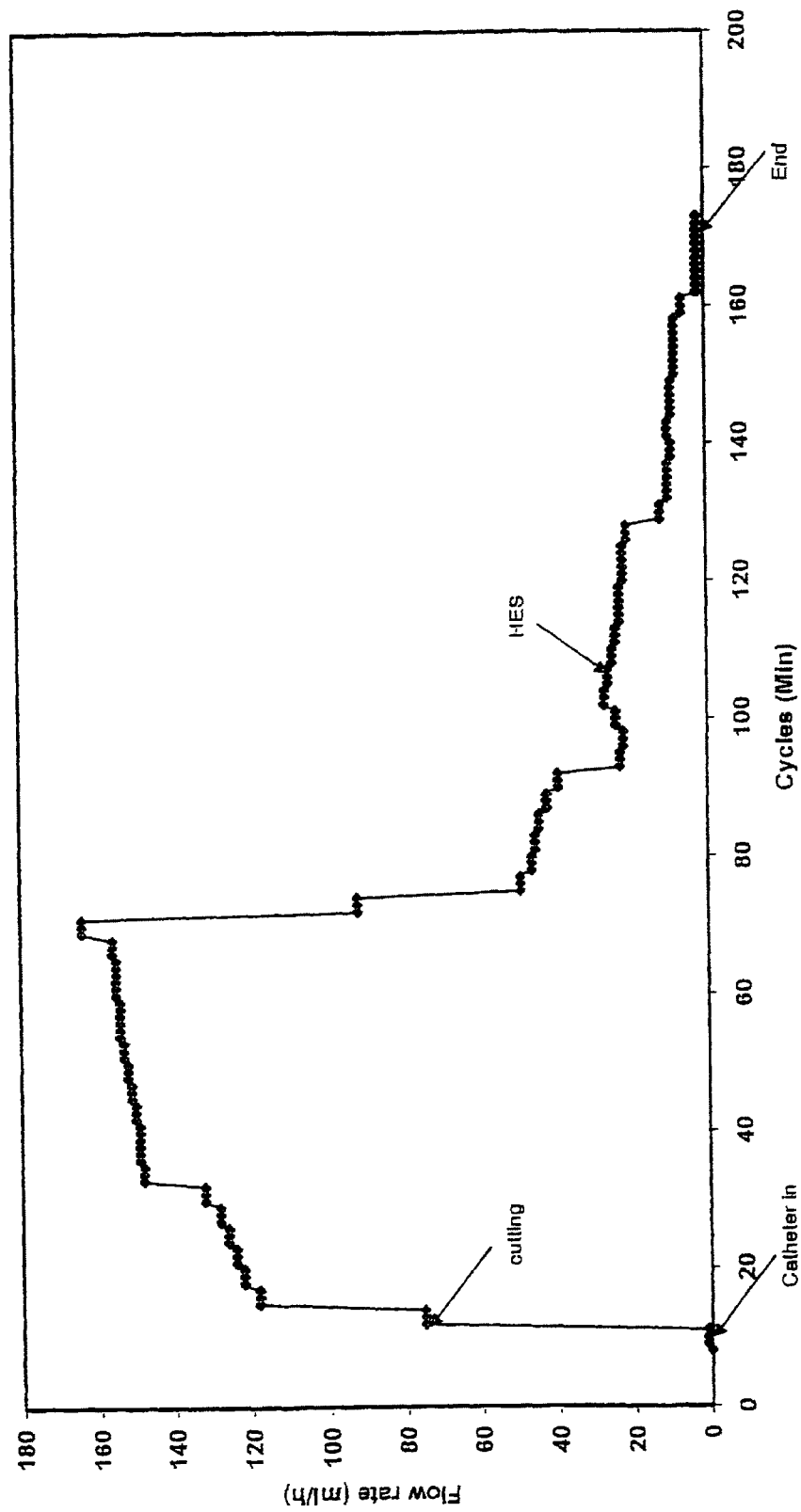
FIG. 2 is a graphical representation of urine flow measured according to the method of the present invention during open heart surgery of a patient.
Figure 3:
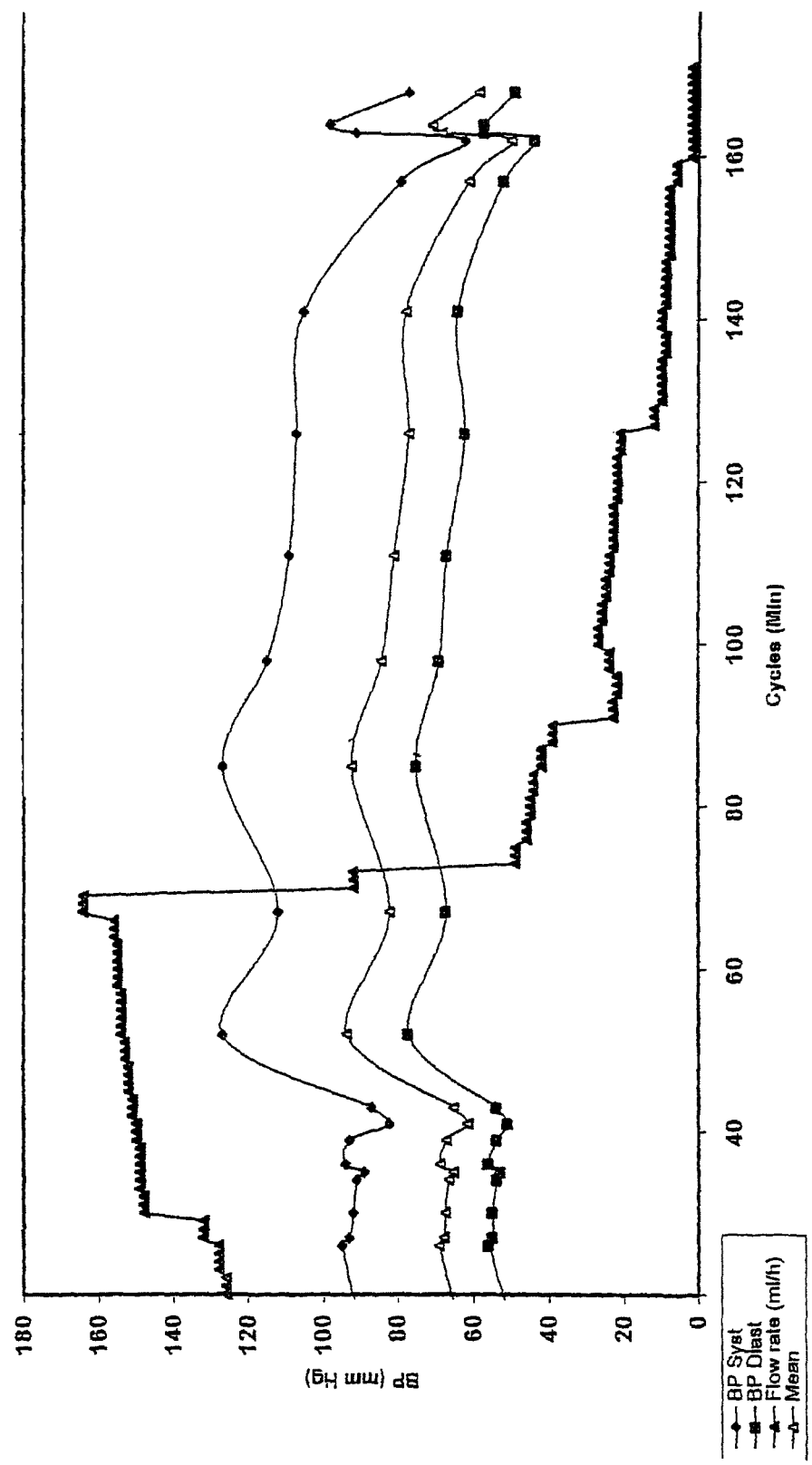
FIG. 3 is a graphical representation of standard blood pressure measurements over time as well as that of urine flow rate according to the present invention taken during open heart surgery.

Referring now to FIGS. 2 and 3, FIG. 2 is a graphical representation of urine flow rate measured according to the method of the present invention and FIG. 3 is a graphical representation of said flow rate on a graph also showing standard blood pressure measurements of the same patient during the same period of time. As will be noted, the method according to the present invention detected and displayed a severe drop in flow rate, more than an hour before a drop was noted by the standard blood pressure measurements.

Thus from FIGS. 1, 2 and 3, it will be noted that the standard methods and tools available indicated that the urine volume continued to increase throughout the procedure and the reduction in flow was detected by the present method more than an hour before the reduction of blood pressure was noted, wherein measurement of blood pressure is used today as the standard for determining fluid status of a patient.

Figure 4:
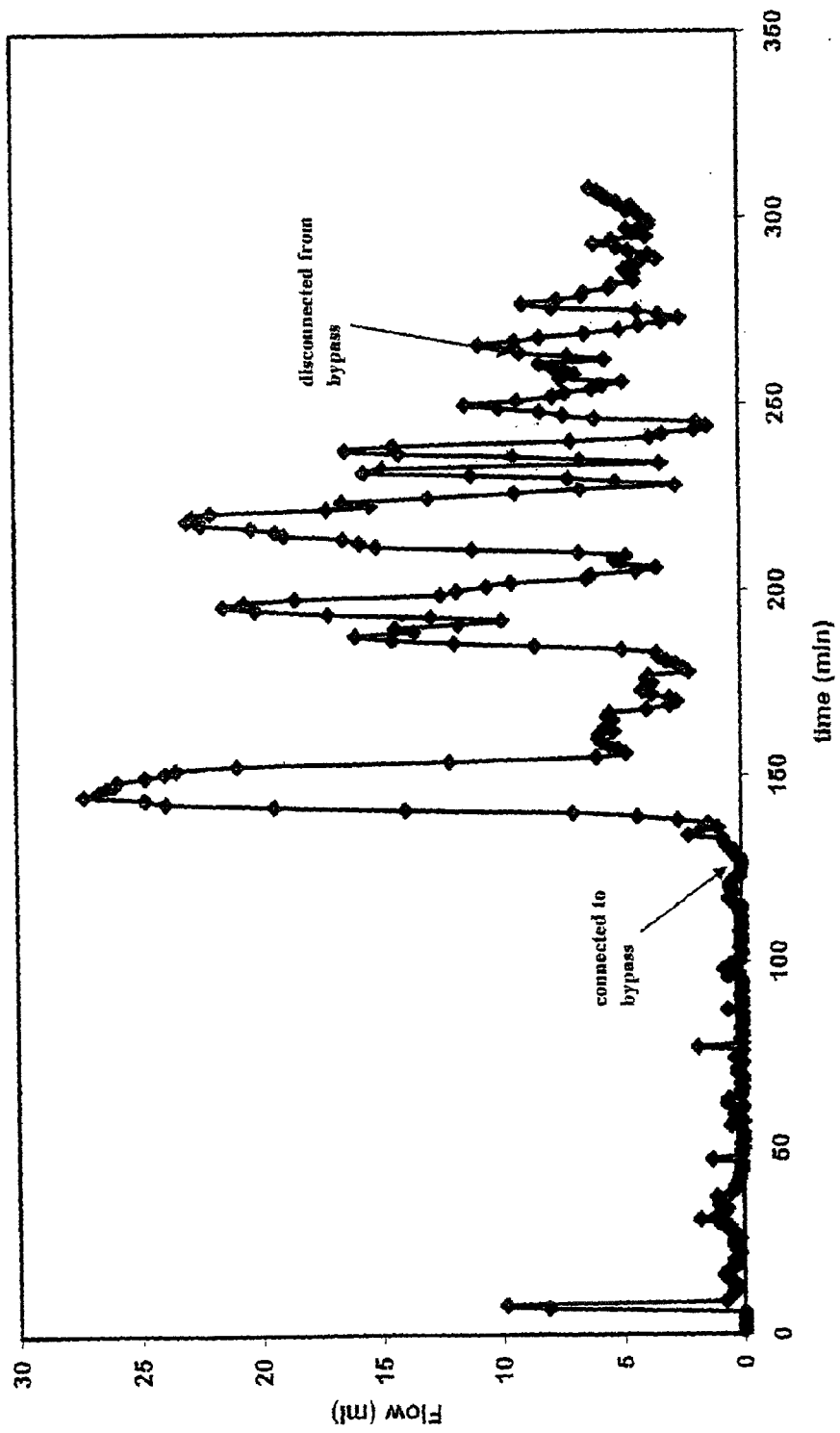
FIG. 4 is a graphical representation of mean flow rate of urine of a patient during bypass open heart surgery.
Figure 5:
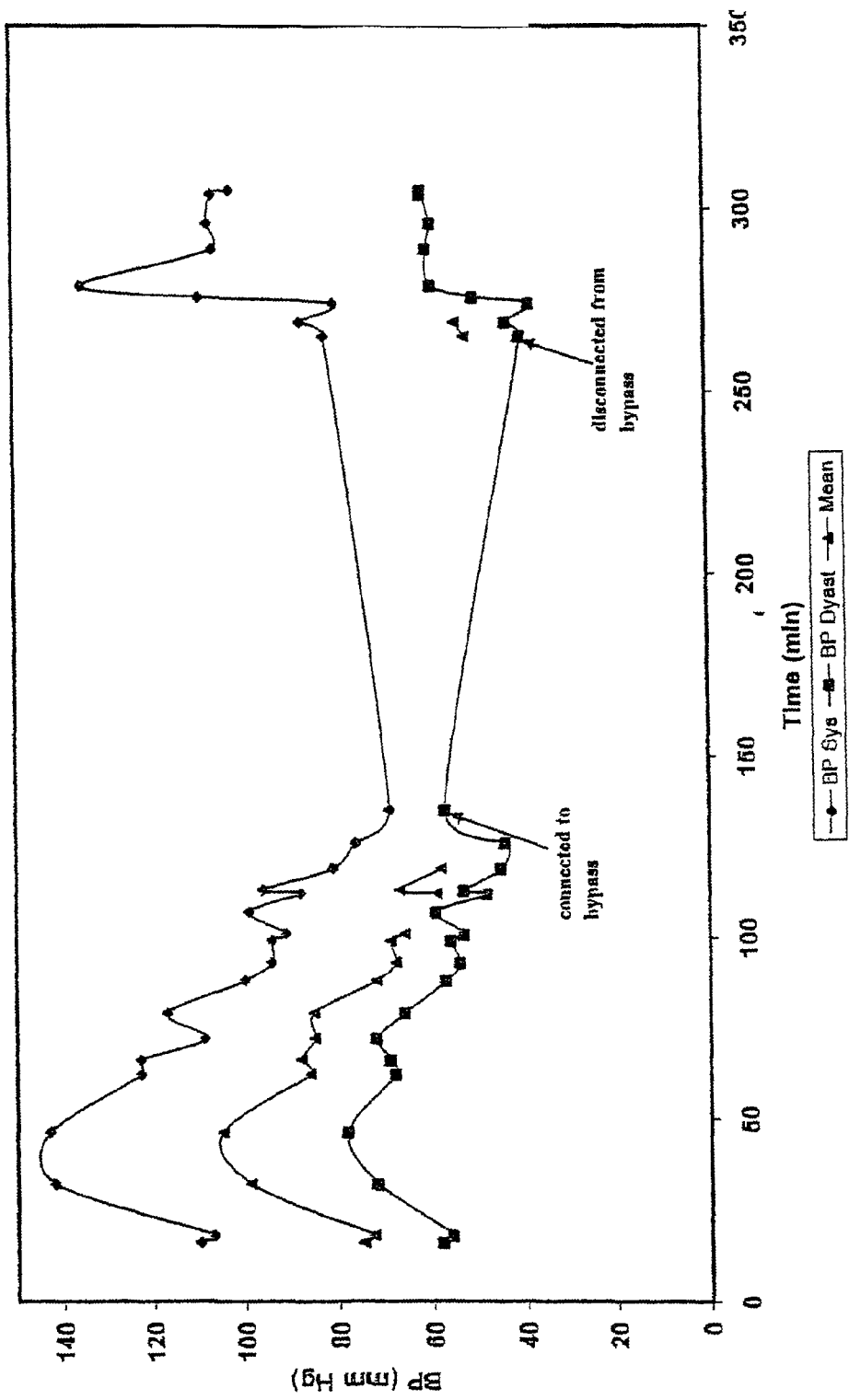
FIG. 5 is a graphical representation of standard blood pressure measurement over time of said patient during said bypass surgery.

Referring now to FIGS. 4 and 5, FIG. 4 records the flow rate of urine as a function of time of a patient undergoing bypass open heart surgery, while FIG. 5 records the standard blood pressure measurements taken of the same patient during the same period of time. As will be noted, FIG. 5 does not show any problem in the blood pressure of the patient, while FIG. 4 which recorded flow rate of urine according to the present invention indicated significant fluctuations in flow, indicating that the patient was not receiving sufficient blood to the kidneys which could have been corrected based on the information provided by the flow rate graph of the present method by increasing cardiac output during bypass.

Figure 6:
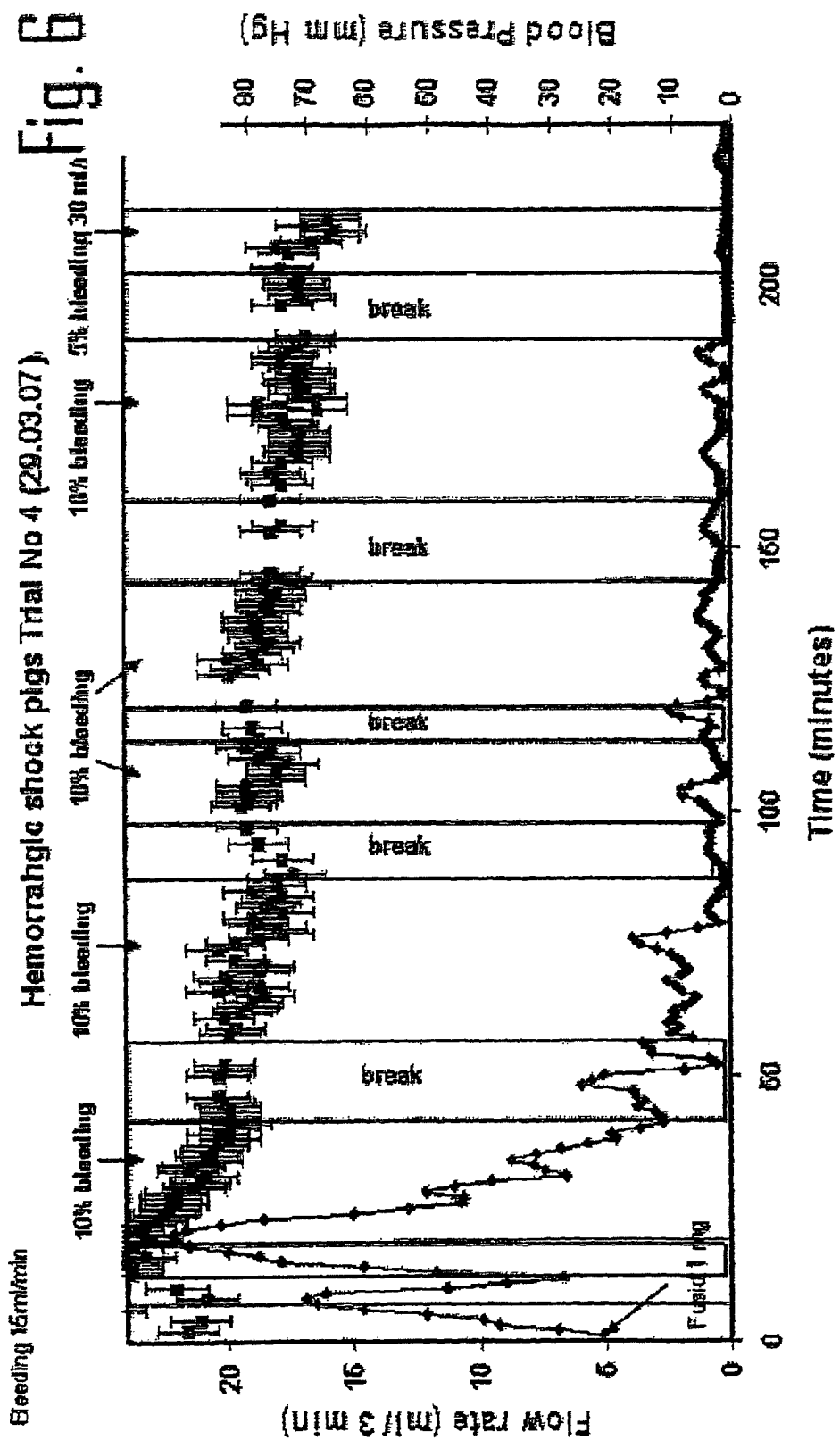
FIG. 6 is a graphical representation of online per minute urine flow rate output as an indication for hemorrhagic shock, as opposed to blood pressure which remains within the range of normal pressure.

Referring to FIG. 6, there is graphically represented the monitoring of a trial of hemorrhagic shock to pigs wherein adult pigs weighing between 50-70 kg were anesthetized and monitored with the first hour serving as a reference, the urinary bladder was pierced and directly catheterized using a foley catheter and then the pigs were bled with a break between bleeding, each bleeding being of 10% of the blood volume of the pig for four repeated bleedings and the final bleeding being of 5%. A diuretic was administered prior to the test and the flow rate against time in minutes was monitored.

As will be noted, the urine flow drops drastically after the first few minutes of bleeding and after 180 minutes, the urine flow goes to 0. At this point, vasoconstriction occurs, cutting off blood to the kidney. The nephrons will be damaged shortly thereafter. As noted however, the blood pressure remains within the normal range after 45% of the blood has been removed from the pigs.

Figure 7:
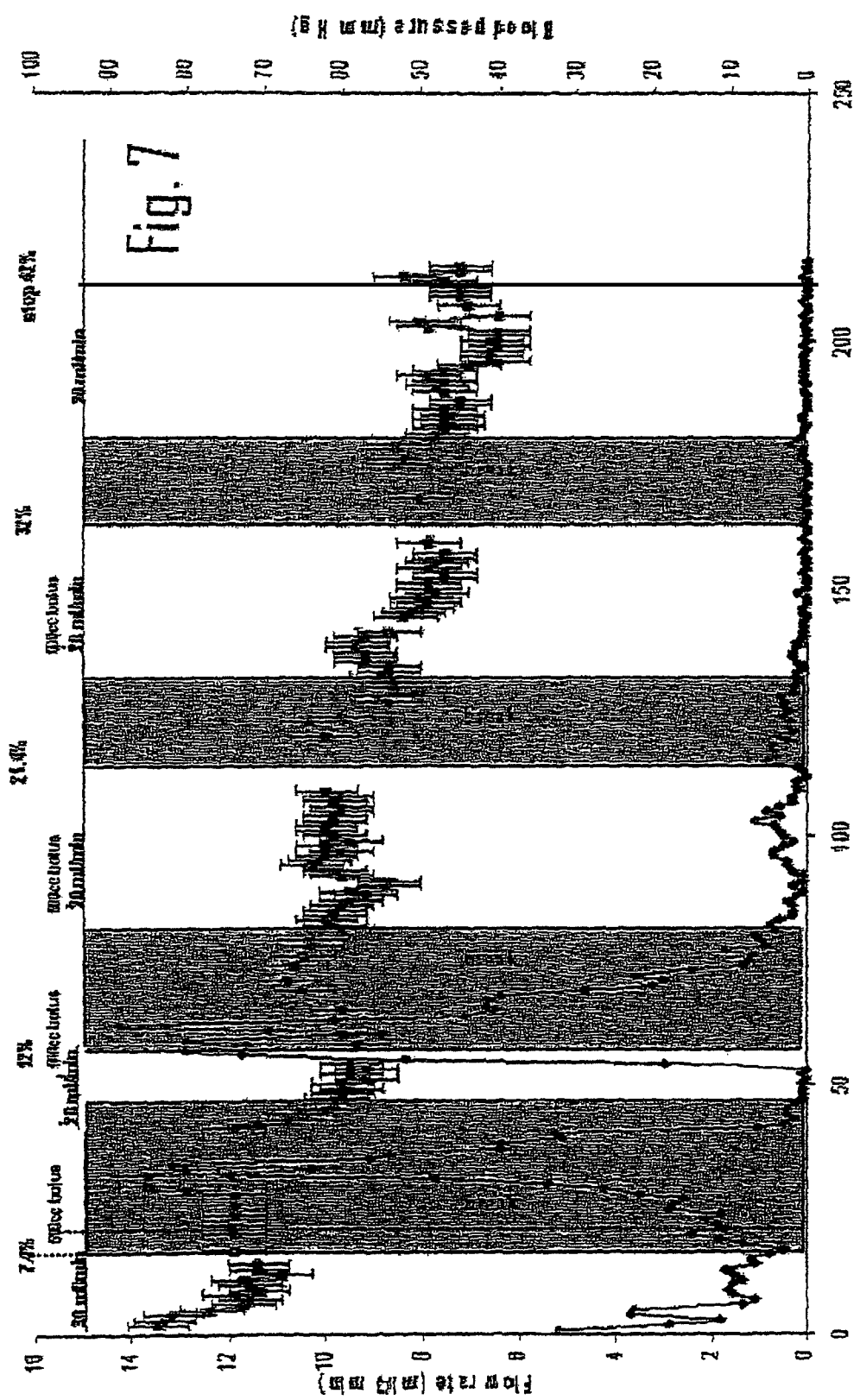
FIG. 7 is a graphical representation of flow rate versus time, as well as blood pressure versus time when a bolus of liquid was administered during induction of hemorrhagic shock.

Referring to FIG. 7, the procedure used in FIG. 6 was repeated, however a bolus of 500 ml of water was administered shortly after bleeding was induced. As can be seen the kidney reacted within minutes resulting in increased urine flow during the period of the first bleeding. A second bolus of 500 ml was administered at the outset of bleeding of the second 10%. Once again, the kidney reacted accordingly resulting in increased urine flow. A third bolus of 500 ml was administered at the outset of bleeding of the third 10% however the kidney did not react thereto, indicating that the kidney was no longer functioning at this point.

Figure 8:
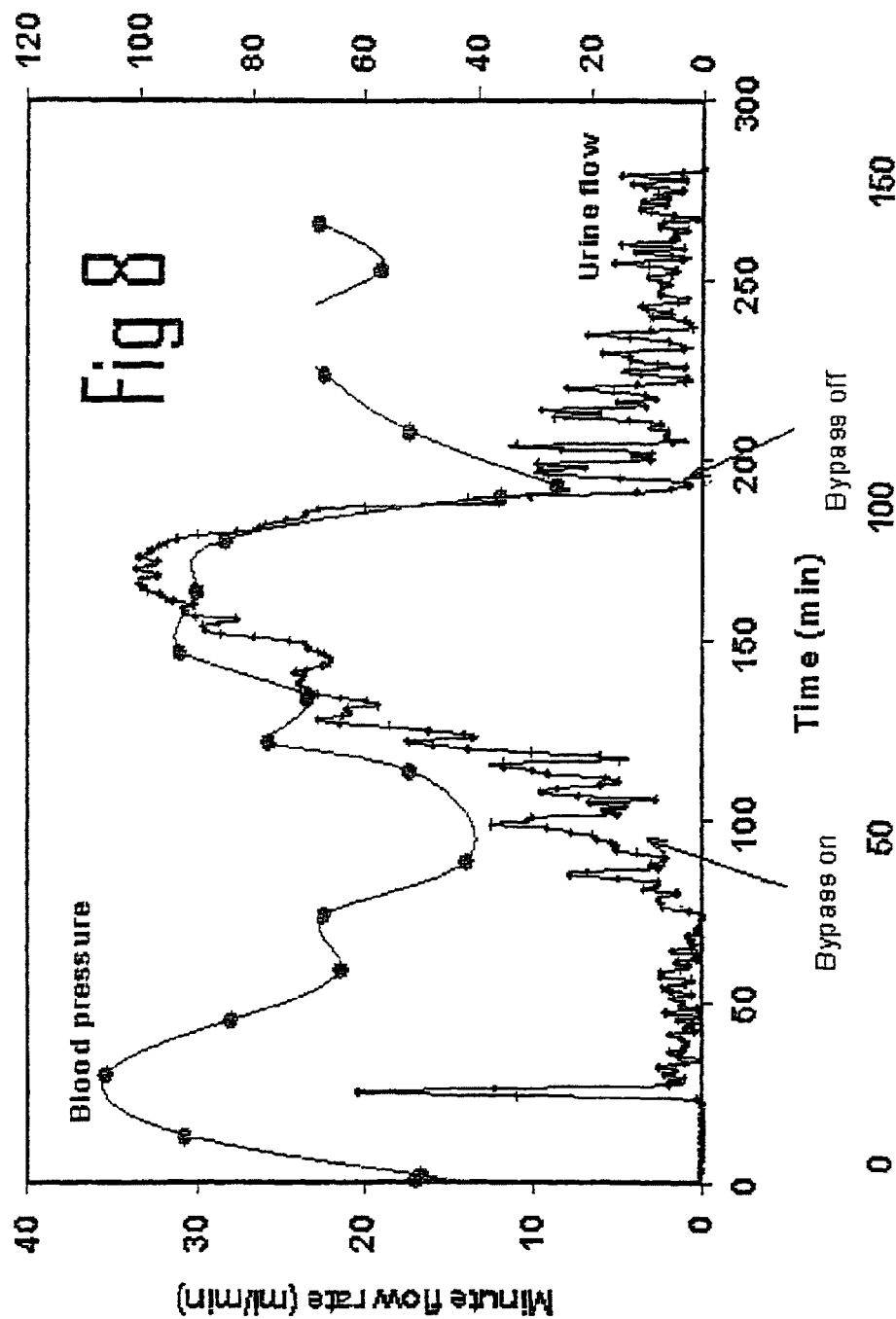
FIG. 8 is a graphical representation of urine flow versus time during bypass surgery.

Referring to FIG. 8, there is seen a graphical representation of urine flow rate as a function of time as well as mean blood pressure during bypass surgery wherein bypass began at minute 100 and ended at around minute 200.

Before commencement of the bypass surgery either a large volume of fluid is administered to the patient or a diuretic is administered or both, in order to maintain kidney activity. As will be noted, urine flow increased in a typical bell shape as seen in the figure. At around minute 200, the operation was completed and the bypass was disconnected. In this case the kidneys were not affected.

Figure 9:
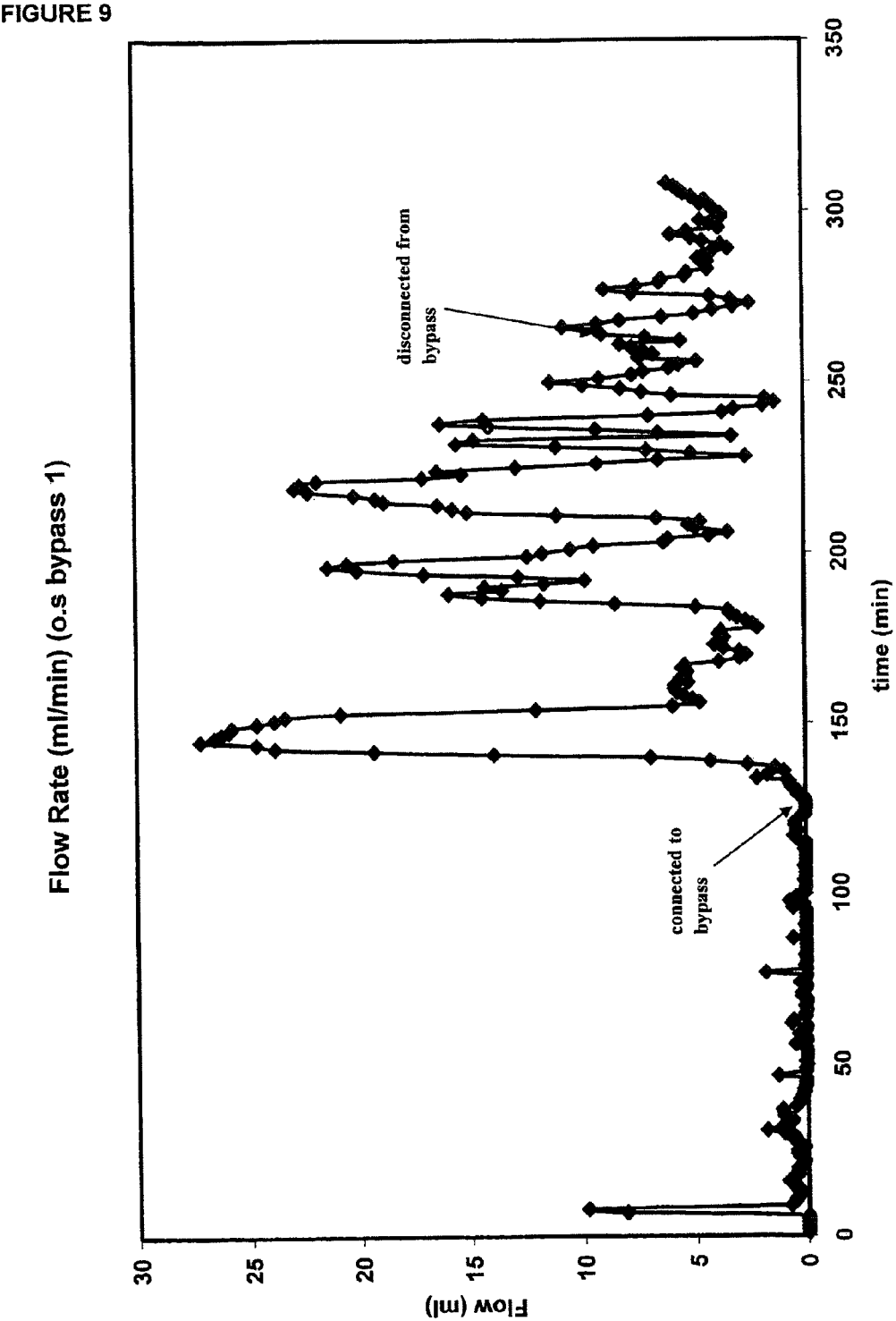
FIG. 9 is a graphical representation of urine flow versus time during bypass surgery in a patient with kidney under stress.

Referring now to FIG. 9, there is seen a further graph of urine flow and mean blood pressure for a different patient undergoing bypass surgery. As will be noted, the urine flow was not smooth and instead was very erratic. This flow pattern which was immediately observable indicated that the kidney was under stress and was damaged and that the patient had acute kidney injury (AKI).

As will be realized, by observing urine flow during surgery, the flow pattern will show the kidney state and indicate when the kidney gets into stress enabling the surgeon to effect early intervention and immediately attempt corrective action.

Figure 10:
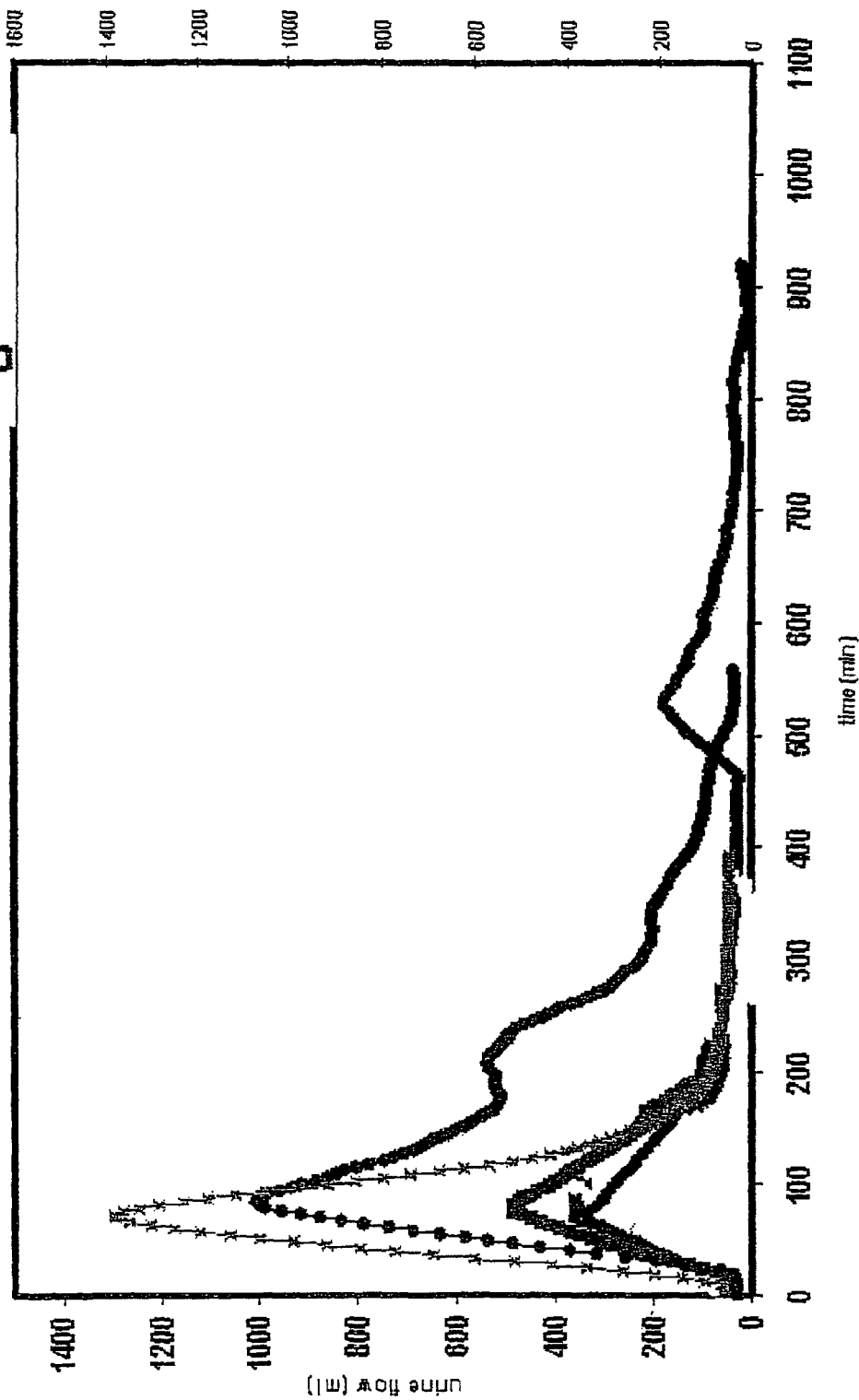
FIG. 10 is a graphical representation of online per minute urine flow rate output after administration of a diuretic medication to different patients with different kidney status.

Referring to FIG. 10, there are seen the patterns of urine flow as a function of time of different patients to whom a diuretic medication was administered. It will be noted that the degree of kidney injury will give different flow peaks. Thus a normal kidney will give a very high peak while a damaged kidney will give a very low peak.

Figure 11:
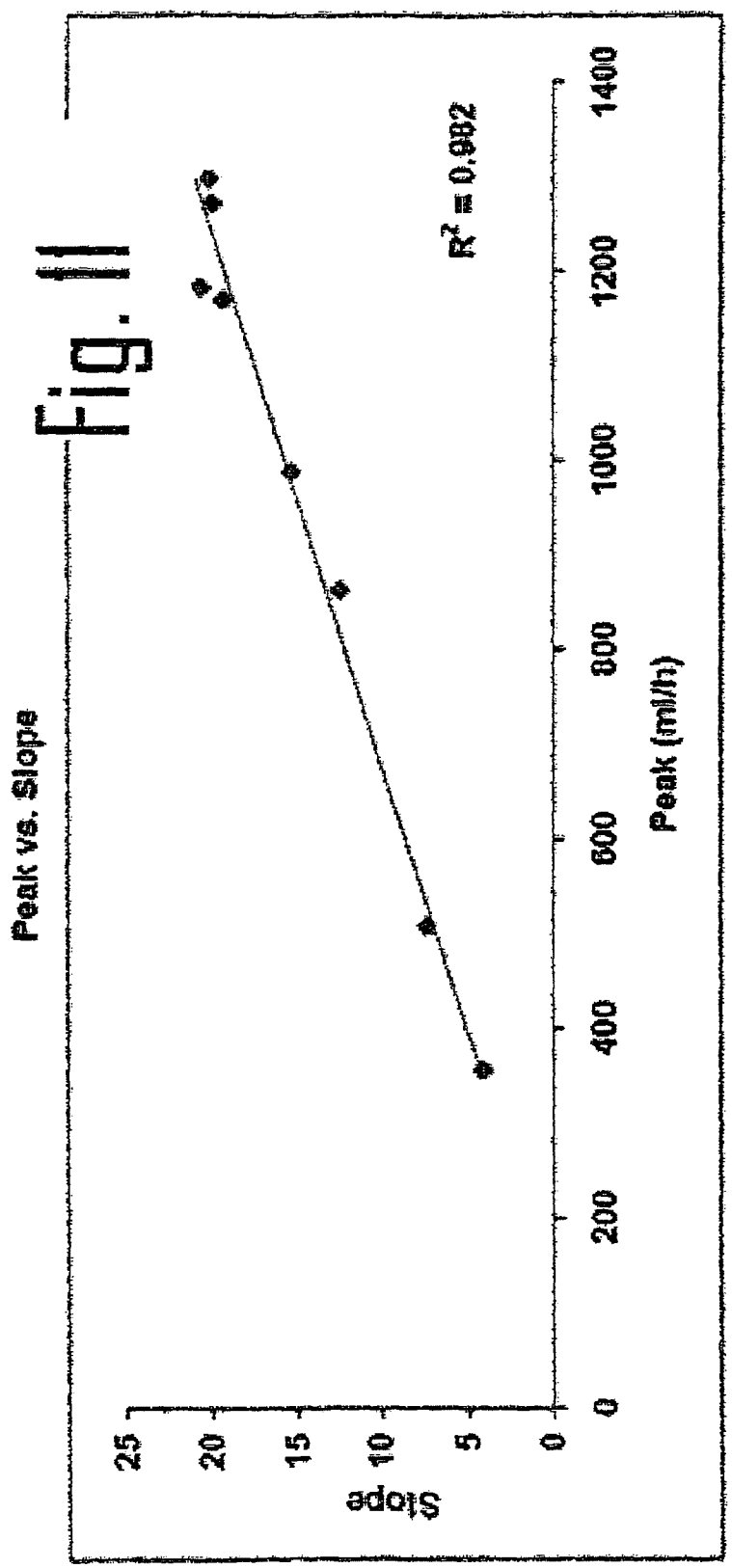
FIG. 11 is a graphical representation of urine flow versus time after administration of a diuretic from which it can be noted that the flow slope and the flow peak are proportional.

Referring to FIG. 11, there is seen a graphical representation of urine flow per minute after administration of a diuretic from which it can be seen that the slope is substantially linear and proportional to the peak and therefore its path can be extrapolated within several minutes after administration of the diuretic thereby providing a very valuable early assessment tool for kidney function.

Referring to FIG. 12, there is seen a graph of a urine flow slope as a function of a diuretic dose of fusid. It will be noted that after 40 mg of diuretic the drug has no further effect thus indicating that it is not necessary to administer high drug doses and that a drug dose of less than 50 mg is sufficient.

Since diuretic drugs such as fusid are nephrotoxic, this finding enables the determination of optimum effective doses of similar drugs, and obviates the administration of excess drugs which are harmful to the body.

Thus, by observing urine flow parameters, optimal amount of drugs can be determined and administered.

Referring to FIG. 13, there is seen a graphical representation of urine flow versus time.

It will be noted that when a patient or body is in a stable state and the fluids administered to the body are constant, a healthy kidney is in a condition that it can produce urine flow at a constant rate. When a small bolus of fluid is administered to the body, the kidney reacts within minutes to remove the fluid and return the body to the original steady state.

Thus, the apparatus of the present invention provides an invaluable tool for early detection of abnormal conditions not provided by the standard measuring tools available today, and has multiple uses in body hydration and kidney management.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A diagnostic method comprising: connecting a catheter of a catheterized patient to a low flow metering device, wherein said low flow metering device incorporates a drop generator and a droplet counter, continuously monitoring urine output and urine flow rates of said catheterized patient by measuring real time minute fluctuations in renal flow and renal output by measuring drops of urine by said drop generator and droplet counter; transmitting said real time minute fluctuations in renal flow and renal output to means which calculate a change of urine output per minute units to correlate with at least one of renal perfusion, renal function, fluid status, polyuria, oleguria, hypoperfusion, hemorrhage shock and GFR; and graphically displaying through a display said minute fluctuations in renal flow and renal output, wherein calculating said change of urine output per minute units comprises calculating a slope.

2. A diagnostic method according to claim 1 for detection of a disease affiliated with abnormal body fluid status.

3. A diagnostic method according to claim 2, wherein said disease is affiliated with hypoperfusion.

4. A diagnostic method according to claim 2, wherein said disease is affiliated with hyperperfusion.

5. A diagnostic method according to claim 1, further comprising providing alarm means.

6. A diagnostic method according to claim 1, comprising continuously monitoring and transmitting urine flow rates per minute units of a catheterized patient to means which correlate the slope of urine output per minute units with at least one of renal perfusion, renal function, fluid status, polyuria, oleguria, hypoperfusion, hemorrhage shock and GFR.

7. A diagnostic method according to claim 6, comprising administering a diuretic to a catheterized patient and monitoring and displaying the slope of urine output per minute after administration thereof.

8. A diagnostic method according to claim 6, comprising administering fluid to a catheterized patient and monitoring and displaying the slope of urine output per minute unit after administration thereof and observing a parameter selected from the slope, a peak and a total time for the flow of urine to return to steady state flow in order to determine a state of the kidney.

9. The method of claim 8, wherein said administering said fluid comprises administering a predetermined amount of fluid.

10. A diagnostic method comprising: connecting a catheter of a catheterized patient to a low flow metering device, wherein said low flow metering device incorporates a drop generator and a droplet counter, continuously monitoring urine output and urine flow rates of said catheterized patient by measuring real time minute fluctations in renal flow and renal output by measuring drops of urine by said drop generator and droplet counter; transmitting said real time minute fluctations in renal flow and renal output to means which calculate a change of urine output per minute units to correlate with at least one of renal perfusion, renal function, fluid status, polyuria, oleguria, hypoperfusion, hemorrhage shock and GFR; and graphically displaying through a display said minute fluctations in renal flow and renal output for determining the hemodynamic state of a patient, further comprising administering a bolus of fluid to the patient and monitoring and displaying urine flow reaction to said bolus to determine the state of hydration and hemorrhagic shock.

11. A diagnostic method which comprises continuous monitoring and measuring of urine output and urine flow of a catheterized patient which method includes linking the output of said device with means which correlate a slope of urine output per minute units with at least one of renal perfusion, renal function, fluid status, polyuria, oleguria, hypoperfusion, hemorrhage shock and GFR.

12. A system for management of a hemodynamic state and kidney function of a body comprising a low flow metering device connected to a catheter inserted into the body by measuring real time minute fluctations in renal flow and renal output by measuring drops of urine by said drop generator and droplet counter; wherein said low flow metering device transmits said real time minute fluctations in renal flow and renal output to monitoring means which calculate a slope of urine output per minute units and to displaying means which display the slope of urine output and urine flow rates per minute units, further comprising means which correlate the slope of urine output per minute units with at least one of renal perfusion, renal function, fluid status, polyuria, oleguria, hypoperfusion, hemorrhage shock and GFR.

13. The system according to claim 12, which monitors and measures urine output and urine flow of a catheterized patient after the administration of a diuretic.

14. The system according to claim 12, which monitors and measures urine output and urine flow of a catheterized patient after the administration of a bolus of fluid to a patient in a stable steady state with a constant fluid input and output.

15. The system of claim 12, wherein the output of said device is linked to means which monitor and display the slope of urine output and urine flow rates per minute units during surgery.

16. The system of claim 12, wherein the output of said device is linked to means which monitor and display the slope of urine output and urine flow rates per minute units after administration of a nephrotoxic drug.

17. The system of claim 12, wherein the output of said device is linked to means which monitor and display the slope of urine output and urine flow rates per minute units during administration of a nephrotoxic drug.

\* \* \* \* \*

UNITED STATES PATENT AND TRADEMARK OFFICE
CERTIFICATE OF CORRECTION

PATENT NO. : 8,663,128 B2  Page 1 of 1
APPLICATION NO. : 12/514835
DATED : March 4, 2014
INVENTOR(S) : Paz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1142 days.

Signed and Sealed this

Twenty-ninth Day of September, 2015

Michelle K. Lee
*Director of the United States Patent and Trademark Office*